(12) United States Patent  
Watanabe et al.

(10) Patent No.: US 6,495,578 B1
(45) Date of Patent: Dec. 17, 2002

(54) SULFONAMIDE DERIVATIVES HAVING OXADIAZOLE RINGS

(75) Inventors: Fumihiko Watanabe, Osaka (JP); Yoshinori Tamura, Osaka (JP); Yasuhiko Fujii, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/959,008

(22) PCT Filed: Apr. 13, 2000

(86) PCT No.: PCT/JP00/02404

§ 371 (c)(1),
(2), (4) Date: Oct. 17, 2001

(87) PCT Pub. No.: WO00/63194

PCT Pub. Date: Oct. 26, 2000

(30) Foreign Application Priority Data

Apr. 19, 1999 (JP) ............................................ 11-110321

(51) Int. Cl.[7] ................ A61K 31/4196; A61K 31/4406; C07D 413/04; C07D 413/14; C07D 271/06
(52) U.S. Cl. ........................ 514/364; 514/340; 548/131; 546/269.4
(58) Field of Search ....................... 548/131; 546/269.4; 514/340, 364

(56) References Cited

FOREIGN PATENT DOCUMENTS

| EP | 0757037 | * | 5/1997 |
| EP | 0 950 656 A1 | | 10/1999 |
| EP | 1 029 541 A1 | | 8/2000 |
| JP | WO99/04780 | * | 4/1999 |
| US | WO98/03166 | * | 1/1998 |

* cited by examiner

Primary Examiner—Joseph K. McKane
Assistant Examiner—Rebecca Anderson
(74) Attorney, Agent, or Firm—Foley & Lardner

(57) ABSTRACT

Sulfonamide derivatives having a matrix metalloprotease inhibiting effect, which are compounds represented by general formula (I), optical isomers of the same, pharmaceutically acceptable salts of both, or solvates of them:

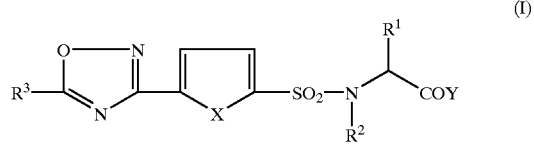

wherein $R^1$ and $R^2$ are each independently hydrogen atom, optionally substituted lower alkyl or the like; $R^3$ is optionally substituted aryl, optionally substituted heteroaryl or the like; X is —CH=CH—, —O—, or —S—; Y is NHOH, hydroxy, or lower alkyloxy.

22 Claims, No Drawings

SULFONAMIDE DERIVATIVES HAVING OXADIAZOLE RINGS

This is a 371 of International Application PCT/JP00/02404 with international filing date of Apr. 13, 2000.

TECHNICAL FIELD

This invention relates to sulfonamide derivatives having oxadiazole rings and metalloproteinase inhibitors containing the same.

BACKGROUND ART

An extracellular matrix, consisting of collagen, fibronectin, laminin, proteoglycan, etc., has a function to support tissues, and plays a role in propagation, differentiation, adhesion, or the like in cells. Metalloproteinases which are protease having a metal ion in the active center, especially matrix metalloproteinases (MMP), are concerned with the degradation of the extracellular matrix. Many types of MMP, from MMP-1 to MMP-23, have been reported as enzymes working for the growth, remodeling of tissues, etc. under usual physiological conditions. It is reported, however, that the progression of various kinds of diseases involving breakdown and fibrosis of tissues (e.g., osteoarthritis, rheumatoid arthritis, corneal ulceration, periodontitis, metastasis and invasion of tumor, and virus infection (HIV infection)) is related with increase of the manifestation or activity of the above-mentioned enzyme. A number of MMP inhibitors tend to have a TNF-α production inhibiting effect.

MMP inhibitors having an oxadiazole ring skeltone are described in WO99/04780.

Compounds, having a similar side chain to those of the present invention and a MMP inhibiting effect, are described in WO97/27174 and the like.

DISCLOSURE OF INVENTION

The inhibiting of such activities of MMP is considered to contribute to the improvement and prevention of the above diseases caused by or related to the activity. Therefore, the development of MMP inhibitors has been desired.

In the above situation, the inventors of the present invention have found that certain sulfonamide derivatives having oxadiazole rings have a potent activity to inhibit MMP.

The present invention relates to:

I) A compound of the formula (I):

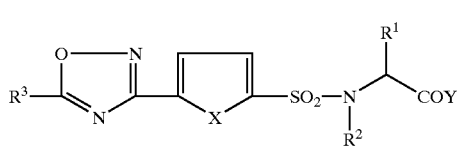

(I)

wherein

R$^1$ and R$^2$ are each independently hydrogen atom, optionally substituted lower alkyl, optionally substituted aryl, optionally substituted aralkyl, optionally substituted heteroaryl, or optionally substituted heteroarylalkyl;

R$^3$ is optionally substituted lower alkyl, optionally substituted cycloalkyl, lower alkyloxy, optionally substituted aryl, optionally substituted aralkyl, optionally substituted heteroaryl, optionally substituted heteroarylalkyl, optionally substituted non-aromatic heterocyclic group, unsubstituted or substituted amino, or halogen;

X is —CH=CH—, —O—, or —S—; and

Y is —NHOH, hydroxy, or lower alkyloxy, its optically active substance, its pharmaceutically acceptable salt, or its solvate.

In more detail, the invention relates to the following II)–XX).

II) A compound of the formula (II):

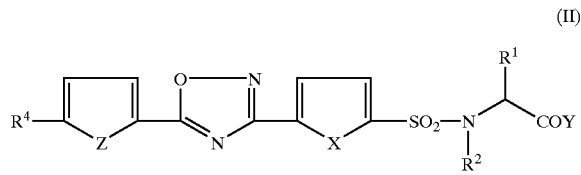

(II)

wherein

R$^1$, R$^2$, X and Y are as defined in I):

R$^4$ is hydrogen atom, optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino group, azo group, or optionally substituted ureide; and Z is —CH=CH—, —O—, or —S—, its optically active substance, its pharmaceutically acceptable salt, or its solvate.

III) A compound of the formula (III):

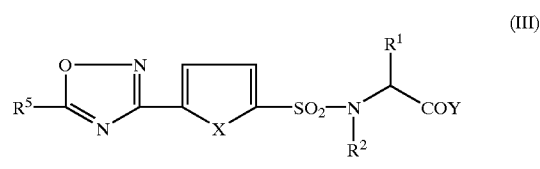

(III)

wherein

R$^1$, R$^2$, X, and Y are as defined in I); and

R$^5$ is optionally substituted alkyl, optionally substituted aralkyl, optionally substituted heteroarylalkyl, lower alkyloxy, unsubstituted or substituted amino, or halogen, its optically active substance, its pharmaceutically acceptable salt, or its solvate.

Preferable a compound is, wherein X is —CH=CH— or —S—; R$^5$ is optionally substituted alkyl or optionally substituted aralkyl; R$^1$ is optionally substituted lower alkyl, optionally substituted aralkyl, or optionally substituted heteroarylalkyl; R$^2$ is hydrogen atom; Y is hydroxy.

IV) A compound of any one of I)–III), wherein Z and X are each independently —CH=CH— or —S—, its optically active substance, its pharmaceutically acceptable salt, or its solvate.

V) A compound of the formula (IV):

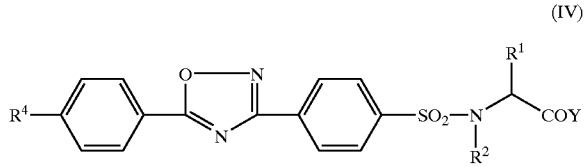

(IV)

wherein
R¹, R², and Y are as defined in I), and R⁴ is as defined in II), its optically active substance, its pharmaceutically acceptable salt, or its solvate.

VI) A compound of the formula (V):

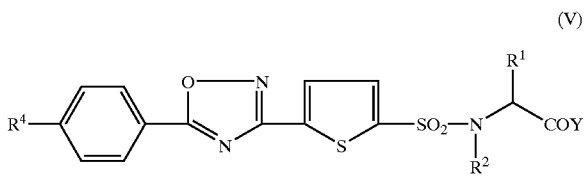

(V)

wherein
R¹, R², and Y are as defined in I), and R⁴ is as defined in II), its optically active substance, its pharmaceutically acceptable salt, or its solvate.

VII) A compound of the formula (VI):

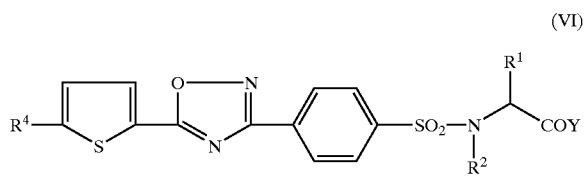

(VI)

wherein
R¹, R², and Y are as defined in I), and R⁴ is as defined in II), its optically active substance, its pharmaceutically acceptable salt, or its solvate.

VIII) A compound of the formula (VII):

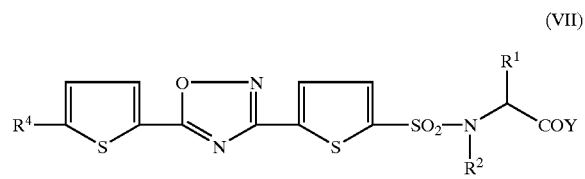

(VII)

wherein
R¹, R², and Y are as defined in I), and R⁴ is as defined in II), its optically active substance, its pharmaceutically acceptable salt, or its solvate.

IX) A compound of any one of I) to VIII), wherein Y is hydroxy, its optically active substance, its pharmaceutically acceptable salt, or its solvate.

X) A compound of any one of I) to IX), wherein R² is hydrogen atom, its optically active substance, its pharmaceutically acceptable salt, or its solvate.

XI) A compound of any one of I) to X), wherein R¹ is hydrogen atom, optionally substituted lower alkyl, optionally substituted aralkyl, or optionally substituted heteroarylalkyl, its optically active substance, its pharmaceutically acceptable salt, or its solvate.

XII) A compound of any one of I)~XI), wherein R¹ is hydrogen atom, methyl, isopropyl, isobutyl, n-butyl, 2-methylthioethyl, phenylmethyl, or indol-3-ylmethyl, its optically active substance, its pharmaceutically acceptable salt, or its solvate.

XIII) A pharmaceutical composition containing a compound of any one of I)~XII).

XIV) A composition for inhibiting metalloproteinase containing a compound of any one of I)~XII).

XV) A composition for inhibiting matrix metalloproteinase containing a compound of any one of I)~XII).

XVI) A composition for treating or preventing cancer which contains a compound of any one of I)~XII).

XVII) A composition for treating or preventing nephritis which contains a compound of any one of I)~XII)

XVIII) A composition for treating or preventing osteoarthritis which contains a compound of any one of I)~XII).

XIX) A composition for treating or preventing cardiac insufficiency which contains a compound of any one of I)~XII).

XX) A composition for treating or preventing rheumatoid arthritis which contains a compound of any one of claims I)~XII).

In the present specification, the term "lower alkyl" employed alone or in combination with other terms means a straight- or branched chain monovalent hydrocarbon group having 1 to 8 carbon atom(s). Examples of the alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like. C1 to C6 alkyl is preferred. C1 to C3 alkyl is more preferred.

The term "alkenyl" employed alone or in combination with other terms in the present specification means a straight- or branched chain monovalent hydrocarbon group having 2 to 8 carbon atoms and at least one double bond. Examples of the alkenyl include vinyl, allyl, propenyl, crotonyl, isopentenyl, a variety of butenyl isomers and the like. C2 to C6 alkenyl is preferred. C2 to C4 alkenyl is more preferred.

The term "lower alkynyl" used in the present specification means a straight or branched chain monovalent hydrocarbon group having 2 to 8 carbon atoms and at least one triple bond. The alkynyl may contain (a) double bond(s). Examples of the alkynyl include ethynyl, 2-propynyl, 3-butynyl, 4-pentynyl, 5-hexynyl, 6-heptynyl, 7-octynyl and the like. C2 to C6 alkynyl is preferred. C2 to C4 alkynyl is more preferred.

The term "cycloalkyl" used in the present specification includes cycloalkyl group having 3 to 8 carbon atoms. Examples of cycloalkyl group include cyclopropyl, cyclobutyl, cyclopentyl, cyclohexyl, cycloheptyl, cyclooctyl and the like. C3 to C6 cycloalkyl is preferred.

In the present specification, the term "aryl" employed alone or in combination with other terms includes monocyclic or condensed ring aromatic hydrocarbons. Examples include phenyl, 1-naphtyl, 2-naphtyl, anthryl, and the like.

The term "aralkyl" herein used means the above mentioned "lower alkyl" substituted with the above mentioned "aryl" at any possible position. Examples of the aralkyl are benzyl, phenylethyl (e.g., 2-phenethyl and the like), phenylpropyl (e.g., 3-phenylpropyl and the like), naphthylmethyl (e.g., 1-naphthylmethyl and 2-naphthylmethyl and the like), anthrylmethyl (e.g., 9-anthrylmethyl and the like), and the like. Benzyl and phenylethyl are preferred.

In the present specification, the term "heteroaryl" employed alone or in combination with other terms includes a 5 to 6 membered aromatic heterocyclic group which contains one or more hetero atoms selected from the group consisting of oxygen, sulfur, and nitrogen atoms in the ring and may be fused with cycloalkyl, aryl, non-aromatic heterocyclic group, and other heteroaryl at any possible position. Examples of the heteroaryl are pyrrolyl (e.g., 1-pyrrolyl, 2-pyrrolyl, 3-pyrrolyl), furyl (e.g., 2-furyl, 3-furyl), thienyl (e.g., 2-thienyl 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl(e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolyl (2-isoindolyl), indolyl (e.g., 1-indolyl, 2-indolyl, 3-indolyl), indazolyl (e.g., 3-indazolyl), puriyl (e.g., 8-puriyl), quinolizinyl (e.g., 2-quinolizinyl), isoquinolyl (e.g., 3-isoquinolyl), quinolyl (e.g., 3-quinolyl, 5-quinolyl), phthalazinyl (e.g., 1-phthalazinyl), naphthyridinyl (e.g., 2-naphthyridinyl), quinolanyl (2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 3-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl) and the like.

Preferable are indole, imidazole, and benzothiazole as "heteroaryl" for $R^1$.

Preferable are thienyl, furyl, and pyridyl as "heteroaryl" for $R^2$.

Preferable are thienyl, furyl, pyridyl and pyrrolyl as "heteroaryl" for $R^3$. More preferred is furyl.

The term "heteroarylalkyl" herein used includes the above mentioned "lower alkyl" substituted with the above mentioned "heteroaryl" at any possible position. Examples of the heteroarylalkyl are thiazolylmethyl (e.g., 4-thiazolylmethyl), thiazolylethyl (e.g., 2-(thiazol-5-yl)ethyl), benzothiazolylmethyl (e.g., (benzothiazol-2-yl)methyl), indolylmethyl (e.g., indol-3-ylmethyl), imidazolylmethyl (e.g., 4-imidazolylmethyl), indazolylmethyl (e.g., 1-indazolylmethyl), benzotriazolylmethyl (e.g., 1-benzotriazolylmethyl), benzoquinolylmethyl (e.g., 2-benzoquinolylmethyl), benzimidazolylmethyl (e.g., 2-benzimidazolylmethyl), pyridylmethyl (e.g., 4-pyridylmethyl), and the like.

Preferable are indol-3-ylmethyl and imidazol-5-ylmethyl as "heteroarylalkyl" for $R^1$.

Preferable are 2-thienyl, 2-furyl and 3-pyridyl as "heteroaryl" for $R^2$.

In the present specification, the term "non-aromatic heterocyclic group" employed alone or in combination with other terms includes a 5 to 7 membered non-aromatic ring which contains one or more hetero atoms selected from the group consisting of oxygen, sulfur, and nitrogen atoms in the ring and a condensed ring which are formed with two or more of the non-aromatic ring. Examples of the non-aromatic heterocyclic group are pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidinyl (piperidino, 2-piperidinyl), piperazinyl (e.g., 1-piperazinyl), indolynyl (e.g., 1-indolynyl), isoindolinyl (e.g., isoindolinyl), morpholinyl (e.g., morpholino, 3-morpholinyl), 1,3-benzodioxolyl (e.g., 5-(1,3-benzodioxolyl)) and the like.

Preferable are pyrazolidinyl, piperidinyl, pyrrolinyl, morpholinyl, and 1,3-benzodioxolyl as "non-aromatic heterocyclic group" for $R^3$.

In the present specification, the term "acyl" employed alone or in combination with other terms includes alkylcarbonyl in which alkyl group is the above-mentioned "lower alkyl" and arylcarbonyl in which aryl group is the above-mentioned "aryl". Examples of the acyl are acetyl, propyonyl, benzoyl, and the like. "Lower alkyl" and "aryl" may be substituted respectively with substituents mentioned below.

The term "halogen" herein used means fluoro, chloro, bromo, and iodo. Fluoro, chloro, and bromo are preferred.

The term "lower alkyloxy" herein used are methyloxy, ethyloxy, n-propyloxy, i-propyloxy, n-butyloxy, i-butyloxy, sec-butyloxy, tert-butyloxy, and the like. Methyloxy, ethyloxy, n-propyloxy, i-propyloxy and n-butyloxy are preferred. C1 to C3 alkyloxy is more preferred.

The term "lower alkylthio" herein used are methylthio, ethylthio, and the like. C1 to C3 alkylthio is preferred.

The term "lower alkyloxycarbonyl" herein used are methyloxycarbonyl, ethyloxycarbonyl, n-propyloxycarbonyl, isopropyloxycarbonyl, and the like.

In the present specification, the term "halo(lower)alkyl" employed alone or in combination with other terms includes the above-mentioned "lower alkyl" which is substituted with the above mentioned "halogen" at 1 to 8 positions, preferably, at 1 to 5. Examples of the halo(lower)alkyl are trifluoromethyl, trichloromethyl, difluoroethyl, trifluoroethyl, dichloroethyl, trichloroethyl, and the like. Preferable is trifluoromethyl.

Examples of the term "halo(lower)alkyloxy" herein used are trifluoromethyloxy and the like.

Examples of the term "lower alkylsulfonyl" herein used are methylsulfonyl, ethylsulfonyl and the like. Preferable is methylsulfonyl.

Examples of the term "acyloxy" herein used are acetyloxy, propionyloxy, benzoyloxy and the like.

In the present specification, the term "substituted amino" employed alone or in combination with other terms includes amino substituted with one or two of the above mentioned "lower alkyl", "aralkyl", "heteroarylalkyl" or "acyl". Examples of the optionally substituted amino are methylamino, dimethylamino, ethylmethylamino, diethylamino, benzylamino, acetylamino, benzoylamino and the like. Preferable are methylamino, dimethylamino, ethylmethylamino, diethylamino and acetylamino.

Examples of the term "substituted aminocarbonyl" herein used are methylaminocarbonyl, dimethylaminocarbonyl, ethylmethylaminocarbonyl, diethylaminocarbonyl and the like. Preferable is diethylaminocarbonyl.

The substituents of "optionally substituted lower alkyl" are cycloalkyl hydroxy, lower alkyloxy, mercapto, lower alkylthio, halogen, nitro, cyano, carboxy, lower alkyloxycarbonyl, halo(lower)alkyl, halo(lower)alkyloxy, substituted or unsubstituted amino, substituted or unsubstituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide and the like. These substituents are able to locate at one or more of any possible positions.

Preferable are mercapto, lower alkylthio, hydroxy, aminocarbonyl, carboxy as substituents of "optionally substituted lower alkyl" for R¹.

Preferable are aminocarbonyl, optionally substituted non-aromatic heterocyclic group as substituents of "optionally substituted lower alkyl" for R².

Preferable are hydroxy, lower alkyloxy, unsubstituted or substituted amino, acyl, optionally substituted non-aromatic heterocyclic group as substituents of "optionally substituted lower alkyl" for R⁵.

The substituents of "optionally substituted cycloalkyl", "optionally substituted aryl", "optionally substituted heteroaryl", "optionally substituted non-aromatic heterocyclic group", "optionally substituted aralkyl", "optionally substituted heteroaryl alkyl", and "optionally substituted ureide" herein used are optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo (lower)alkyloxy, unsubstituted or substituted amino, unsubstituted or substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino group, azo group, or optionally substituted ureide and the like. These substituents are able to locate at one or more of any possible positions.

Preferable are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, aryl, heteroaryl, non-aromatic heterocyclic group, aralkyl and the like, as substituents for R¹ and R² of "optionally substituted aryl", "optionally substituted aralkyl", "optionally substituted heteroaryl", and "optionally substituted heteroaryl alkyl".

Preferable are lower alkyl, cycloalkyl, hydroxy lower alkyl, hydroxy, acyl, lower alkyloxy, lower alkylthio, halogen, nitro, carboxy, cyano, halo(lower)alkyl, halo (lower)alkyloxy, unsubstituted or substituted amino, unsubstituted or substituted aminocarbonyl, heteroaryl, non-aromatic heterocyclic group, and the like as substituents of "optionally substituted cycloalkyl", "optionally substituted aryl", "optionally substituted heteroaryl", and "optionally substituted non-aromatic heterocyclic group" for R³.

BEST MODE FOR CARRYING OUT THE INVENTION

Compounds (I) of the invention are able to be synthesized from natural or unnatural amino acids, their esters or their salts as starting materials in accordance with the procedure described WO97/27174. And it is possible to produce the compounds as follows.

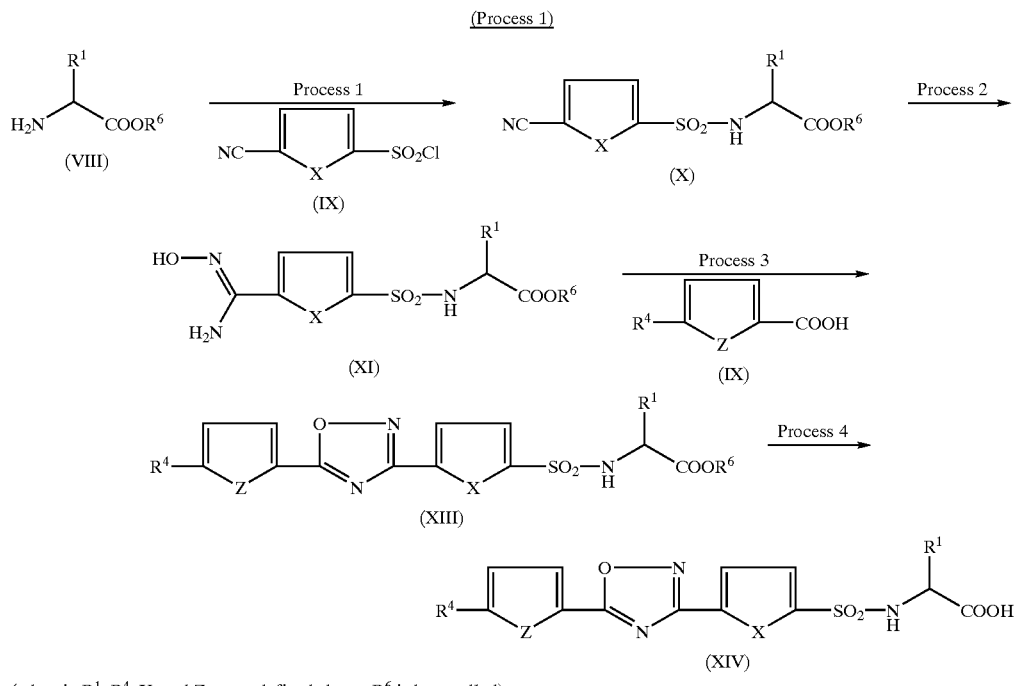

(wherein R¹, R⁴, X, and Z are as defined above, R⁶ is lower alkyl)

This is a process of obtaining sulfonamide derivatives (X) by the reaction of compound (VIII) having an amino group and compound (IX) having a cyano group. The process may be carried out in accordance with the same procedure as (Method A-Process 1) in WO97/27174.

(Process 2)

The present process is a process of obtaining compound (XI) by the reaction of compound (X) having cyano group and hydroxylamine. To a solution of compound (X) and a hydroxyl amine derivative such as of hydroxylamine hydrochloride in ethanol and the like is added a base (e.g., triethylamine) and the mixture is reacted under 10° C. to reflux to obtains the target compound (XI).

(Process 3)

The present process is a process of constructing of an oxadiazole ring by the reaction of compound (XI) and compound (XII) having a carboxy group. This process may be carried out in the same manner as that described in Gui-Bai Liang, Danqing D. Feng, Tetrahedron Letters, 37, 6627 (1996). Another method for the process of construduting the oxadiazole ring by acid chloride is reported (Cuy D. Diana, et al., J. Med. Chem., 1994, 37, 2421–2436). (Process 4)

The present step is a process of yielding the compound (XIV) by hydrolysis of the compound (XIII). This step may be carried out in accordance with a usual method as described in "Protective Groups in Organic Synthesis, Theodora W Green (John Wiley & Sons)" and the like.

The effect of a treating agent of heart failure can be confirmed by the procedure described in WO00/15213.

The effect of a treating agent of nephritis (glomerulopathy) can be confirmed by the procedure described in WO00/04780.

The above effects can be confirmed as follows.

(Animals)

Five to eight weeks old male Slc-Wistar rats were used in the experiment.

(Procedure for the Establishment of Nephritogenic Antibody)

Mouse monoclonal antibodies are established against rat glomeruli and the monoclonal antibodies which induce nephritis are screened as described below.

To induce glomerulonephritis by the injection of antibody, the presence of the antigen on the cell surface is required. First of all, we investigated by immunofluorescence whether or not the obtained monoclonal antibodies accumulate in the glomeruli after the intravenous injection to rats.

The distribution and molecular weight of antigen recognizing each clone of monoclonal antibodies are determined. Furthermore, nephritis-inducing activity is evaluated based on the urinary excretion of protein within a week after single injection of antibody.

During this study, a monoclonal antibody E30 was established (J.J.N., vol. 36, p106, 1994). It has been known that E30 recognizes the surface antigen of mesangial cells by the immunohistochemical study, and that single administration of E30 to rats induces complement-dependent mesangial cell injury. The pathological changes are described below.

E30 antibodies immediately bind to the surface antigens of mesangial cells in glomeruli after a intravenous injection to rats, followed by the activation of complement system within 30 min. And then, degeneration and necrosis of mesangial cells are occurred, resulting in the detachment of glomerular basement membrane from mesangial area. A series of these pathological features is known as mesangiolysis. Accumulation of platelet and infiltration of inflammatory cells such as polymorphonuclear leukocyte and macrophage are observed during mesangiolysis. Mesangiolysis is prominent 1–3 days after the injection of the antibody and mesangial expansion is frequently observed at that time. Proliferation of glomerular cells, mainly mesangial cells, is initiated 3–5 days after the injection, resulting in the morphological features of mesangial proliferative glomerulonephritis by a week. The reconstruction of the glomerular capillary network is accompanied with mitosis and proliferation of mesangial cells and irregular patterns of angiogenesis. After then, increased number of mesangial cells and overproduced extracellular matrix are resolved with time course and the pathological features recover to the normal one by a month.

Thus, since a single injection of the monoclonal antibody induces a reproducible nephritis model, the antibody-induced nephritis model is useful for grasping a basic changes in glomerular disease as a biological response.

In Asia, a half of the patients with glomerulonephritis is diagnosed as IgA nephropathy. IgA nephropathy is characterized as IgA deposition to glomerular mesangial cells. IgA nephropathy belongs to proliferative nephritis caused by immunoreaction against mesangial cell itself. Therefore, the monoclonal antibody-induced nephritis model is also useful for studying the pathogenesis of IgA nephropathy.

In addition, the monoclonal antibody, E30, is available for establishing some chronic nephritis models induced by the combination dosing with puromycin aminonucleoside (J.J.N., vol. 39, p220, 1997) or by a single injection of it to uni-nephrectomized rats (J.J.N., vol. 39, p300, 1997). The preventing or treating effects of test compounds on the development of glomerulosclerosis could be evaluated by utilizing these chronic nephritis models. Similar experiments can be examined by using following methods: 1) methods by using other monoclonal antibodies or anti-thymocyte serum instead of E30, 2) methods by using hereditary nephrosis rats or mice, 3) methods by using spontaneously diabetic rats or mice, and 4) methods by using streptozotocin- or alloxan-induced diabetic rats or mice.

(Protocol for Assay)

In order to induce glomerulonephritis, E30 of 20 to 500 $\mu$g, preferably 50 to 200 $\mu$g, is intravenously injected to rats of five to eight weeks old. Test compounds of 0.1 to 500 mg, preferably 1 to 200 mg, are suspended with 3 to 10%, preferably 4 to 6%, gum arabic solution and the like, and are orally given 1 to 5 hours, preferably 1.5 to 3 hours, prior to E30 injection. Constant amount of test compounds are then consecutively given 1 to 3 times a day. Evaluation of test compounds are determined by the amount of urinary protein excretion 2 days after E30 injection when proteinuria reaches to the maximum level.

As for some compounds which exhibit antiproteinuric effects in the method described above, the amount of urinary protein excretion during 5 to 8 days, changes in body weight, morphological changes in glomeruli by autopsy, inhibitory ratio of mesangial proliferation and renal function are assessed after the treatment of these compounds.

Determination of the amount of urinary protein excretion is performed by the collection of 24-hour urine samples with stainless metabolic cages followed by the measurement of the concentration of urinary protein. Blood samples obtained at the follow-up period are processed for the determination of blood urea nitrogen and plasma creatinine, which indicate renal function. As a marker of damaged renal tubules, urinary amounts of N-acetyl-D-glycosaminidase excretion is measured. Furthermore, to study the inhibitory effects of compounds on mesangial proliferation following E30 injection, the number of PCNA (proliferating cell nuclear antigen) positive cells per single glomerulus is counted. Morphological changes are observed with light and electron microscopy.

The term "solvate" includes, for example, solvates with organic solvents, hydrates, and the like.

The term "compound of the present invention" herein used includes a pharmaceutically acceptable salt or solvate thereof. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, mallein acid, fumaric acid, benzenesulfonic acid, p-toluenesulfonic acid, and the like). These salts can be formed by the usual method. These hydrates can coordinate with any water molecules.

The compound of the present invention is not restricted to any particular isomers but includes all possible isomers and racemic modifications.

The compound of the present invention has an excellent activity for inhibiting MMP-2 and inhibits matrix dissolution, as described in the following test example.

Definitely, the compounds of the present invention are useful in the prevention or treatment of diseases such as osteoarthritis, rheumatoid arthritis, corneal ulceration, periodontal disease, advanced virus infection (e.g., HIV), arteriosclerosis obliterans, arteriosclerotic aneurysm, atherosclerosis, restenosis, sepsis, septic shock, coronary thrombosis, aberrant angiogenesis, scleritis, multiple sclerosis, open angle glaucoma, retinopathies, proliferative retinopathy, neovascular glaucoma, pterygium, keratitis, epidermolysis bullosa, psoriasis, diabetes, nephritis (glomerulopathy), neurodegengerative disease, inflammation, osteoporosis, deossification, gingivitis, tumor growth, tumor angiogenesis, ocular tumor, angiofibroma, hemangioma, fever, hemorrhage, coagulation, cachexia, anorexia, acute infection, shock, autoimmune disease, malaria, Crohn disease, meningitis, heart failure, asthmatic respiratory tract disease, arteriosclerosis, and gastric ulcer. The compounds are expected especially as nephritis (glomerulopathy).

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 0.01 to 100 mg/kg/day, and preferably 0.1 to 30 mg/kg/day for adult.

The following examples are provided to further illustrate the present invention and are not to be constructed as limiting the scope thereof, Abbreviations described below are used in the following examples.

Me: methyl
Et: ethyl
$^n$Pr: n-propyl
i-Pr: isopropyl
$^n$Bu: n-butyl
i-Bu: isobutyl
$^n$Hex: n-hexyl
c-Hex: cyclohexyl
Ac: acetyl
Bn: benzyl
DMSO: dimethylsulfoxide

EXAMPLE

Example 1

The Preparation of the Compound (A-1)

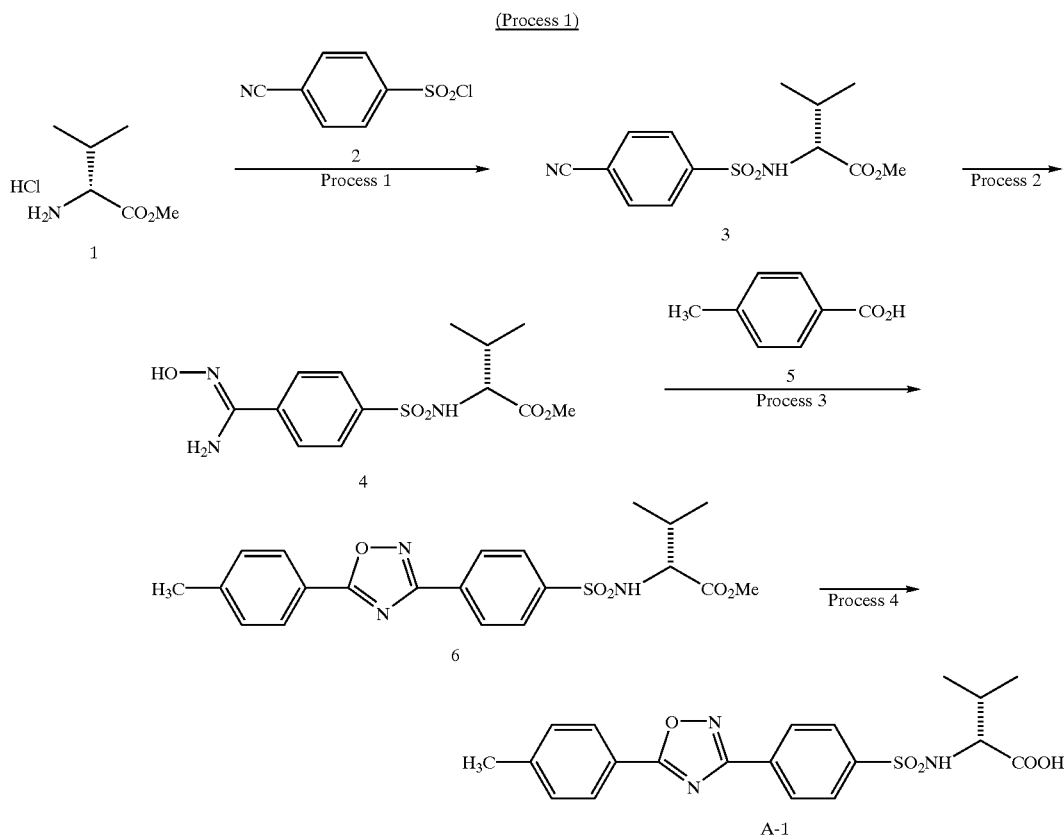

To a suspension of D-valine methyl ester hydrochloride (1) (2.2 g, 13.1 mmol) in tetrahydrofuran (40 ml) were added N-methylmorpholine (3.9 mL, 35.5 mmol) and 4-cyanobenzenesulfonyl chloride (2) (2.4 g, 11.9 mmol) at room temperature. After the mixture was stirred for 1.5 h, the reaction mixture was poured into ice-2N-hydrochloric acid and was extracted with ethyl acetate twice. The organic layer was washed with 5% aqueous sodium bicarbonate and water, dried over anhydrous sodium sulfate, and concentrated in vacuo to obtain light brown oil product. Crystallization from ethyl ether/n-hexane gave compound (3) (white granular crystal, 3.12 g). Yield=88%. Mp=54–57° C.

IR vmax(cm$^{-1}$)(KBr):3292, 2974, 2231, 1732, 1709, 1348, 1173.

$^1$H-NMR(δ ppm)(CDCl$_3$) 0.87(d, 6.8 Hz, 3H), 0.97(d, J=6.8 Hz, 3H), 2.09(m, 1H), 3.51(s, 3H), 3.80(dd, J=4.9, 10.2 Hz, 1H), 5.25(d, J=10.2 Hz, 1H), 7.80(d, J=8.4 Hz, 2H), 7.96(d, J=8.8 Hz, 2H).

Elemental analysis (%) C$_{13}$H$_{16}$N$_2$O$_4$S

Calcd.: C,52.69; H, 5.44; N, 9.45; S, 10.82. Found: C, 52.80; H, 5.34; N, 9.52; S, 10.55.

$[\alpha]^{23}_D$+4.7±0.9(0.506%, DMSO)

(Process 2)

To a suspension of compound (3) (3.24 g, 10.9 mmol) and hydroxylamine hydrochloride (0.91. g, 13.1 mmol) in ethanol (100 ml) was added triethylamine (1.83 ml) and the mixture was stirred under reflux for 2.5 h. After ethanol was evaporated, water was added and the residue was extracted with ethyl acetate. The organic layer was washed with saturated brine, dried over anhydrous sodium sulfate and then evaporated in vacuo. The residue was recrystallized from ethyl acetate/n-hexane to obtain compound (4) (white columnar crystals, 3.4 g). Yield=94%. Mp=130–131° C.

IR(KBr, vmax cm$^{-1}$) 3485, 1722, 1651, 1335, 1165.

$^1$H-NMR(δ ppm)(CDCl$_3$) 0.87(d, J=7.0 Hz, 3H), 0.95(d, J=7.0 Hz, 3H), 2.04(m, 1H), 3.46(s, 3H), 3.77(dd, J=4.9, 10.2 Hz, 1H), 5.04(br s, 2H), 5.44(d, J=10.2 Hz, 1H), 7.76(d, J=8.8 Hz, 2H), 7.85(d, J=8.2 Hz, 2H).

Elemental analysis (%) C$_{13}$H$_{19}$N$_3$O$_5$S

Calcd.: C,47.40; H, 5.81; N, 12.76; S, 9.73. Found: C, 47.60; H, 5.76; N, 12.47; S, 9.76.

$[\alpha]^{23}_D$+8.8±1.0(0.503%, DMSO)

(Process 3)

To a solution of the compound (4) (500 mg, 1.52 mmol) and p-methylbenzoic acid (207 mg; 1.52 mmol) in di(ethyleneglycol) dimethyl ether (5 ml) was added 1-ethyl-3-(3-dimethylaminopropyl)carbodiimide hydrochloride (349 mg, 1.82 mmol), and the reaction mixture was heated under stirring at 50° C. for 2 h and at 110° C. for 6 h. The reaction mixture was poured into water and extracted with ethyl acetate. The organic layer was washed with water, dried over anhydrous sodium sulfate, and concentrated in vacuo. 1.54 g of the obtained orange residue was subjected to silica gel column chromatography, and the fraction eluted with ethyl acetate/n-hexane=⅓ was collected, recrystallized from ethyl acetate/n-hexane to yield compound (5) (white needle crystals, 338 mg). Yield=52%, Mp=157–159° C.

IR(KBr, vmax cm$^{-1}$) 3288, 2967, 1739, 1410, 1348, 1169, 1136.

$^1$H-NMR(δ ppm)(CDCl$_3$) 0.89(d, J=6.6 Hz, 3H), 0.97(d, J=7.0 Hz, 3H), 2.06(m, 1H), 2.47(s, 3H), 3.46(s, 3H), 3.81(dd, J=4.9 Hz, 9.8 Hz, 1H), 5.16(d, J=9.8 Hz, 1H), 7.37(d, J=8.2 Hz, 2H), 7.97(d, J=8.8 Hz, 2H), 8.11(d, J=8.0 Hz, 2H), 8.31(d, J=8.8 Hz, 2H)

Elemental analysis (%) C$_{21}$H$_{23}$N$_3$O$_5$S

Calcd.: C,58.72; H, 5.40; N, 9.78; S, 7.47 Found: C, 58.63; H, 5.26; N, 9.83; S, 7.54

$[\alpha]^{23}_D$+7.3±0.9(0.504%, DMSO)

(Process 4)

To a solution of compound (5) (304 mg, 0.71 mmol) in 8.5 ml of dimethyl sulfoxide was added 1N-sodium hydroxide solution (2.1 ml, 2.1 mmol) at room temperature and then stirred for 15 h. The reaction mixture was poured into water and acidified with 2N-hydrochloric acid and then was extracted with ethyl acetate twice. The organic layer was washed with water, dried over anhydrous sodium sulfate, and concentrated in vacuo. 0.38 g of the obtained white residue was recrystallized with acetone/n-hexane to yield compound A-1 (white needle crystal 220 mg). Yield=75%, Mp=208–209° C.

IR(KBr, vmax cm$^{-1}$): 3334, 2970, 1730, 1714, 1691, 1614, 1410, 1350, 1174, 1136.

Elemental analysis (%) C$_{20}$H$_{21}$N$_3$O$_5$S

Calcd.: C, 57.82; H, 5.10; N, 10.12; S, 7.72 Found: C, 57.72; H, 5.06; N, 10.04; S, 7.84

$[\alpha]^{24}_D$−12.1±1.0(0.505%, DMSO)

Compound (A-2) to Compound (A-67) and Compound (B-1) to Compound (B-16) were synthesized in a manner similar to Example 1.

Their physical data were shown in Tables 1 to 12.

TABLE 1

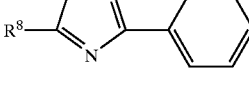

| Ex. No. | Compound No. | R$^7$ | R$^8$ | * | $^1$H-NMR (DMSO-d$_6$) |
|---|---|---|---|---|---|
| 1 | A-1 | i-Pr | Me-⟨phenyl⟩- | R | 0.81(d, J=6.9Hz, 3H), 0.85(d, J=6.9 Hz, 3H), 1.97(m, 1H), 2.45(s, 3H), 3.59(m, 1H), 7.50(d, J=8.1Hz, 2H), 7.99(d, J=9.0Hz, 2H), 8.11(d, J=8.1 Hz, 2H), 8.25(d, J=8.7Hz, 2H), 12.64(br s, 1H) |

TABLE 1-continued

Structure: $R^8$-[1,2,4-oxadiazole]-C$_6$H$_4$-SO$_2$NH-C*H(R$^7$)-CO$_2$H

| Ex. No. | Compound No. | R$^7$ | R$^8$ | * | $^1$H-NMR (DMSO-d$_6$) |
|---|---|---|---|---|---|
| 2 | A-2 | i-Pr | 4-Cl-C$_6$H$_4$- | R | 0.81(d, J=6.9Hz, 3H), 0.85(d, J=6.9 Hz), 1.97(m, 1H), 3.59(m, 1H), 7.77 (d, J=8.7Hz, 2H), 8.00(d, J=8.7Hz, 2H), 8.23(d, J=8.7Hz, 2H), 8.26(d, J=8.7Hz, 2H), 8.20–8.30(1H), 12.63 (br s, 1H) |
| 3 | A-3 | i-Pr | 4-Et-C$_6$H$_4$- | R | 0.83(t, J=6.8Hz, 6H), 1.24(t, J=7.8 Hz, 3H), 1.97(m, 1H), 2.75(q, J=7.4 Hz, 2H), 3.59(m, 1H), 7.53(d, J=8.4 Hz, 2H), 7.99(d, J=8.4Hz, 2H), 8.13 (d, J=8.0Hz, 2H), 8.26(d, J=8.8Hz, 2H), 8.20–8.30(1H), 12.64(br s, 1H) |
| 4 | A-4 | i-Pr | 4-n-Bu-C$_6$H$_4$- | R | 0.83(t, J=6.8Hz, 6H), 0.92(t, J=7.3 Hz, 3H), 1.33(m, 2H), 1.62(m, 2H), 1.97(m, 1H), 2.72(t, J=8.0Hz, 2H), 3.59(m, 1H), 7.51(d, J=8.4Hz, 2H), 7.99(d, J=8.4Hz, 2H), 8.12(d, J=8.4 Hz, 2H), 8.25(d, J=8.4Hz, 2H), 8.20–8.30(1H), 12.63(br s, 1H) |
| 5 | A-5 | Bn | 4-Me-C$_6$H$_4$- | R | 2.45(s, 3H), 2.75(dd, J=9.0, 13.5Hz, 1H), 2.98(dd, J=5.4, 13.5Hz, 1H), 3.97(m, 1H), 7.1–7.3(m, 5H), 7.50(d, J=7.8Hz, 2H), 7.76(d, J=8.4Hz, 2H), 8.11(d, J=8.1Hz, 4H), 8.50(d, J=9.0Hz, 1H), 12.80(br s, 1H) |
| 6 | A-6 | Bn | 4-Cl-C$_6$H$_4$- | R | 2.75(dd, J=9.6, 13.8Hz, 1H), 2.99(dd, J=5.7, 13.8Hz, 1H), 3.96(dt, J=5.4, 9.3Hz, 1H), 7.10–7.22(m, 5H), 7.73–7.79(m, 4H), 8.09–8.14(m, 2H), 8.20–8.26(m, 2H), 8.52(d, J=9.3Hz), 12.80(br s, 1H) |

TABLE 2

| Ex. No. | Compound No. | R$^7$ | R$^8$ | * | $^1$H-NMR (DMSO-d$_6$) |
|---|---|---|---|---|---|
| 7 | A-7 | Bn | 4-F-C$_6$H$_4$- | R | 2.75(dd, J=9.6, 13.5Hz, 1H), 2.99(dd, J=4.8, 13.5Hz, 1H), 3.96(dt, J=5.1, 9.3Hz, 1H), 7.10–7.22(m, 5H), 7.54 (t, J=8.4Hz, 2H), 7.76(d, J=8.4Hz, 2H), 8.12(d, J=8.4Hz, 2H), 8.29(dd, J=5.4, 8.4Hz, 2H), 8.52(d, J=9.3Hz, 1H), 12.80(br s, 1H) |
| 8 | A-8 | Bn | 4-Me$_2$N-C$_6$H$_4$- | R | 2.75(dd, J=9.6, 13.5Hz, 1H), 2.9–3.0 m, 1H), 3.02(s, 6H), 3.97(m, 1H), 6.86(d, J=8.7Hz, 2H), 7.1–7.2(m, 5 H), 7.78(d, J=8.7Hz, 2H), 7.91(d, J= 8.7Hz, 2H), 8.18(d, J=8.7Hz, 2H), 8.58(d, J=7.5Hz, 1H), 12.80(br s, 1H) |
| 9 | A-9 | Bn | 4-$^n$Bu-C$_6$H$_4$- | R | 0.92(t, J=7.5Hz, 3H), 1.33(m, 2H), 1.02(quintet, J=7.5Hz, 2H), 2.72(t, J=7.5Hz, 2H), 2.74(m, 1H), 2.98(dd, J=5.4Hz, 5.4, 13.8Hz, 1H), 3.95 (m, 1H), 7.1–7.2(m, 5Hz), 7.51(d, J= 8.4Hz, 2H), 7.76(d, J=8.4Hz, 2H), 8.12(d, J=8.4Hz, 2H), 8.12(d, J=8.4 Hz, 2H), 8.49(d, J=8.1Hz, 1H), 12.78(br s, 1H) |

TABLE 2-continued

| Ex. No. | Compound No. | R⁷ | R⁸ | * | ¹H-NMR (DMSO-d₆) |
|---|---|---|---|---|---|
| 10 | A-10 | Me | Me—C₆H₄— | R | 1.20(d, J=7.2Hz, 3H), 2.44(s, 3H), 3.86(m, 1H), 7.49(d, J=8.1Hz, 2H), 7.98–8.03(m, 2H), 8.11(d, J=8.1Hz, 2H), 8.37(d, J=7.5Hz, 1H), 12.65(br s, 1H) |
| 11 | A-11 | Me | Cl—C₆H₄— | R | 1.20(d, J=7.2Hz, 3H), 3.86(m, 1H), 7.74–7.79(m, 2H), 7.98–8.03(m, 2H), 8.20–8.30(m, 4H), 8.38(d, J=6.9 Hz, 1H), 12.60(br s, 1H) |
| 12 | A-12 | H | Me—C₆H₄— | | 2.45(s, 3H), 3.68(d, J=4.8Hz, 2H), 7.49(d, J=8.1Hz, 2H), 7.98–8.04(m, 2H), 8.07–8.13(m, 2H), 8.24–8.31(m, 3H), 12.70(br s, 1H) |
| 13 | A-13 | H | Cl—C₆H₄— | | 3.68(d, J=3.3Hz, 2H), 7.73–7.79(m, 2H), 7.99–8.05(m, 2H), 8.19–8.31(m, 5H), 12.68(br s, 1H) |
| 14 | A-14 | i-Bu | n-Bu | R | 0.72(d, J=6.6Hz, 3H), 0.82(d, J=6.6 Hz, 3H), 0.93(t, J=6.8Hz, 3H), 1.3–1.5(2H), 1.79(m, 2H), 3.03(t, J=7.2 Hz, 3H), 3.71(m, 1H), 7.94(d, J=8.6 Hz, 2H), 8.17(d, J=8.4Hz, 2H), 8.35 (d, J=9.2Hz, 1H), 12.59(br s, 1H) |

TABLE 3

| Ex. No. | Compound No. | R⁷ | R⁸ | * | ¹H-NMR (DMSO-d₆) |
|---|---|---|---|---|---|
| 15 | A-15 | i-Bu | Me—C₆H₄— | R | 0.73(d, J=6.3Hz, 3H), 0.83(d, J=6.6 Hz, 3H), 1.4–1.5(m, 2H), 1.5–1.7 (m, 1H), 2.45(s, 3H), 3.37(m, 1H), 7.50(d, J=8.4Hz, 2H), 7.98(d, J=8.4 Hz, 2H), 8.11(d, J=8.4Hz, 2H), 8.26 (d, J=8.4Hz, 2H), 8.35(br s, 1H), 12.49(br s, 1H) |
| 16 | A-16 | i-Pr | C₆H₅— | R | 0.82(d, J=6.6Hz, 3H), 0.85(d, J=6.9Hz, 3H), 1.98(m, 1H), 3.60(dd, J=5.7, 9.0Hz, 1H), 7.65–7.73 (m, 2H), 7.77(m, 1H), 8.00(d, J=8.1Hz, 2H), 8.20–8.30(m, 5H), 12.64 (br s, 1H) |
| 17 | A-17 | i-Pr | F—C₆H₄— | R | 0.81(d, J=6.6Hz, 3H), 0.85(d, J=6.9 Hz, 3H), 1.88–2.04(m, 1H), 3.54–3.63(m, 1H), 7.53(t, J=9.0Hz, 2H), 8.00(d, J=8.4Hz, 2H), 8.20–8.35(m, 5H), 12.63(brs, 1H) |
| 19 | A-19 | i-Pr | Me—C₆H₄— | S | 0.81(d, J=6.9Hz, 3H), 0.85(d, J=6.9 Hz, 3H), 1.97(m, 1H), 2.45(s, 3H), 3.59(dd, J=6.0, 8.4Hz, 1H), 7.50(d, J=8.1Hz, 2H), 7.99(d, J=8.1Hz, 2H), 8.11(d, J=8.7Hz, 2H), 8.24(m, 1H), 8.25(d, J=8.7Hz, 2H), 12.65(br, 1H) |
| 20 | A-20 | i-Pr | ⁿPr—C₆H₄— | R | 0.81(d, J=6.6Hz, 3H), 0.85(d, J=6.9 Hz, 3H), 0.93(t, J=7.5Hz, 3H), 1.59–1.73(m, 2H), 1.90–2.04(m, 1H), 2.70(t, J=7.5Hz, 2H), 3.54–3.63(m, 1H), 7.51(d, J=8.4Hz, 2H), 7.99(d, J=8.7Hz, 4H), 8.13(d, J=8.4Hz, 2H), 8.25(d, J=8.7Hz, 2H), 12.63(brs, 1H) |

TABLE 3-continued

| Ex. No. | Coum pound No. | R⁷ | R⁸ | * | ¹H-NMR (DMSO-d₆) |
|---|---|---|---|---|---|
| 21 | A-21 | i-Pr | nPr-phenyl- | S | 0.81(d, J=6.6Hz, 3H), 0.85(d, J=6.9 Hz, 3H), 0.93(t, J=7.5Hz, 3H), 1.59–1.73(m, 2H), 1.90–2.04(m, 1H), 2.70(t, J=7.5Hz, 2H), 3.54–3.63(m, 1H), 7.51(d, J=8.4Hz, 2H), 7.99(d, J=8.7Hz, 4H), 8.13(d, J=8.4Hz, 2H), 8.25(d, J=8.7Hz, 2H), 12.57(brs, 1H) |
| 22 | A-22 | i-Pr | 2-thienyl- | R | 0.81(d, J=6.6Hz, 3H), 0.85(d, J=6.9 Hz, 3H), 1.97(m, 1H), 3.59(dd, J=6.0, 9.0Hz, 1H), 7.39(dd, J=3.9, 5.1Hz, 1H), 7.99(d, J=8.4Hz, 2H), 8.12(dd, J=0.9, 3.9Hz, 1H), 8.15(dd, J=0.9, 5.1Hz, 1H), 8.23(d, J=8.4Hz, 2H), 8.26(d, J=9.0Hz, 1H), 12.63(br s, 1H) |

TABLE 4

| Ex. No. | Coum pound No. | R⁷ | R⁸ | * | ¹H-NMR (DMSO-d₆) |
|---|---|---|---|---|---|
| 23 | A-23 | i-Pr | 2-thienyl- | S | 0.81(d, J=6.6Hz, 3H), 0.85(d, J=6.6 Hz, 3H), 1.97(m, 1H), 3.59(dd, J=6.0, 8.7Hz, 1H), 7.39(dd, J=3.9, 4.8Hz, 1H), 7.98(d, J=8.4Hz, 2H), 8.12(dd, J=1.2, 3.9Hz, 1H), 8.15(dd, J=1.2, 4.8Hz, 1H), 8.23(d, J=8.4Hz, 2H), 8.26 8m, 1H), 12.64(br, 1H) |
| 24 | A-24 | i-Pr | 5-Me-2-thienyl- | R | 0.81(d, J=7.0Hz, 3H), 0.84(d, J=7.0 Hz, 3H), 1.96(m, 1H), 2.6(s, 3H), 3.58(m, 1H), 7.11(dd, J=1.0, 3.6Hz, 1H), 7.94(d, J=4.2Hz, 1H), 7.97(d, J=8.8Hz, 2H), 8.21(d, J=8.4Hz, 2H), 8.26(m, 1H), 12.6(m, 1H) |
| 25 | A-25 | i-Pr | 5-Me-2-thienyl- | S | 0.81(d, J=6.9Hz, 3H), 0.84(d, J=6.9 Hz, 3H), 1.97(m, 1H), 2.60(s, 3H), 3.58(m, 1H), 7.10(dd, J=0.9, 3.6Hz, 1H), 7.94(d, J=3.6Hz, 1H), 7.97(d, J=8.4Hz, 2H), 8.20(d, J=8.4Hz, 2H), 8.25(d, J=8.1Hz, 1H), 12.64(br, 1H) |
| 26 | A-26 | i-Pr | 5-Cl-2-thienyl- | R | 0.81(d, J=6.6Hz, 3H), 0.84(d, J=6.9 Hz, 3H), 1.97(m, 1H), 3.58(m, 1H), 7.46(d, J=3.9Hz, 1H), 7.98(d, J=8.7 Hz, 2H), 8.03(d, J=4.2Hz, 1H), 8.21(d, J=8.7Hz, 2H), 8.27(d, J=9.3 Hz, 1H), 12.64(br s, 1H) |
| 27 | A-27 | i-Pr | 5-Cl-2-thienyl- | S | 0.81(d, J=6.6Hz, 3H), 0.84(d, J=6.6 Hz, 3H), 1.97(m, 1H), 3.58(m, 1H), 7.46(d, J=3.9Hz, 1H), 7.98(d, J=9.0 Hz, 2H), 8.03(d, J=3.9Hz, 1H), 8.21 (d, J=9.0Hz, 2H), 8.26(d, J=6.6Hz, 1H) |
| 28 | A-28 | i-Pr | 3-thienyl- | R | 0.81(d, J=6.9Hz, 3H), 0.85(d, J=6.6 Hz, 3H), 1.98(m, 1H), 3.59(dd, J=6.0, 8.7Hz, 1H), 7.78(dd, J=0.9, 5.1Hz, 1H), 7.90(dd, J=3.0, 5.1Hz, 1H), 7.99(d, J=8.4Hz, 2H), 8.24(d, J=8.4Hz, 2H), 8.26(d, J=8.7Hz, 1H), 8.70(dd, J=0.9, 3.0Hz, 1H), 12.63(br s, 1H) |

TABLE 4-continued

| Ex. No. | Coumpound No. | R⁷ | R⁸ | * | ¹H-NMR (DMSO-d₆) |
|---|---|---|---|---|---|
| 29 | A-29 | Bn | phenyl | R | 2.75(dd, J=9.6, 13.8Hz, 1H), 2.99 (dd, J=5.1, 13.8Hz, 1H), 3.97(dt, J=5.1, 9.0Hz, 1H), 7.11–7.23(m, 5H), 7.66-7.73(m, 2H), 7.74–7.81 (m, 3H), 8.13(d, J=8.1Hz, 2H), 8.20–8.26(m, 2H), 8.53(d, J=9.0Hz, 1H), 12.81(br s, 1H) |

TABLE 5

| Ex. No. | Coumpound No. | R⁷ | R⁸ | * | ¹H-NMR (DMSO-d₆) |
|---|---|---|---|---|---|
| 30 | A-30 | Bn | Me–C₆H₄– | S | 2.45(s, 3H), 2.75(dd, J=9.3, 13.8 Hz, 1H), 2.99(dd, J=5.1, 13.8Hz, 1H), 3.97(m, 1H), 7.12–7.22(m, 5H), 7.50(d, J=8.1Hz, 2H), 7.76 (d, J=8.1Hz, 2H), 8.11(d, J=8.4 Hz, 2H), 8.51(d, J=8.4Hz, 1H), 12.80(br, 1H) |
| 31 | A-31 | Bn | Et–C₆H₄– | R | 1.25(t, J=7.5Hz, 3H), 2.69–2.81(m, 3H), 2.98(dd, J=5.4, 13.5Hz, 1H), 3.96(m, 1H), 7.10–7.23(m, 5H), 7.53 (d, J=8.1Hz, 2H), 7.76(d, J=8.7Hz, 2H), 8.09–8.16(m, 4H), 8.51(d, J=8.7 Hz, 1H), 12.78(br s, 1H) |
| 32 | A-32 | Bn | ⁿPr–C₆H₄– | R | 0.93(t, J=7.2Hz, 3H), 1.59–1.73(m, 2H), 2.70(t, J=7.5Hz, 2H), 2.75(dd, J=9.6, 13.8Hz, 1H), 2.99(dd, J=5.4, 13.8Hz, 1H), 3.96(dt, J=5.4, 8.7Hz, 1H), 7.10–7.23(m, 5H), 7.51(d, J=8.1 Hz, 2H), 7.76(d, J=8.4Hz, 2H), 8.09–8.16(m, 4H), 8.50(d, J=8.7Hz, 1H), 12.78(br s, 1H) |
| 33 | A-33 | Bn | ⁿPr–C₆H₄– | S | 0.93(t, J=7.5Hz, 3H), 1.59–1.73(m, 2H), 2.70(t, J=8.1Hz, 2H), 2.75(dd, J=9.3, 13.8Hz, 1H), 2.98(dd, J=5.4, 13.8Hz, 1H), 3.89–4.02(m, 1H), 7.08–7.23(m, 5H), 7.51(d, J=8.1Hz, 2H), 7.76(d, J=8.1Hz, 2H), 8.12(d, J=8.1 Hz, 2H), 8.13(d, J=8.1Hz, 2H), 8.45–8.58(m, 1H) |
| 34 | A-34 | Bn | NC–C₆H₄– | R | 2.74(dd, J=9.6, 13.6Hz, 1H), 2.99 (dd, J=5.1, 13.9Hz, 1H), 3.97(m, 1H), 7.1–7.25(5H), 7.77(d, J=8.4Hz, 2H), 8.13(d, J=8.4Hz, 2H), 8.16(d, J=8.0Hz, 2H), 8.38(d, J=8.6Hz, 2H), 8.52(d, J=8.8Hz, 1H), 12.81 (m, 1H) |
| 35 | A-35 | Bn | c-Hex–C₆H₄– | R | 1.2–1.55(5H), 1.65–1.95(5H), 2.65(m, 1H), 2.75(dd, J=9.6, 13.8Hz, 1H), 2.98(dd, J=5.7Hz, 13.8Hz, 1H), 3.96(m, 1H), 7.05–7.25(5H), 7.54(d, J=8.1Hz, 2H), 7.76(d, J=8.7Hz, 2H), 8.12(d, J=8.7Hz, 2H), 8.13(d, J=8.1 Hz, 2H), 8.52(d, J=9.3Hz, 1H), 12.8(br s, 1H) |

TABLE 6

| Ex. No. | Compound No. | R⁷ | R⁸ | * | ¹H-NMR (DMSO-d₆) |
|---|---|---|---|---|---|
| 36 | A-36 | Bn | 3,4-dimethylphenyl (Me, Me on benzene) | R | 2.46(s, 3H), 2.75(dd, J=9.3, 13.5Hz, 1H), 2.99(dd, J=5.1, 13.5Hz, 1H), 3.96(dt, J=5.1, 9.0Hz, 1H), 7.11–7.22 (m, 5H), 7.55–7.60(m, 2H), 7.76(d, J=8.7Hz, 2H), 7.98–8.07(m, 2H), 8.12(d, J=8.7Hz, 2H), 8.51(d, J=9.0 Hz, 1H), 12.79(br s, 1H) |
| 37 | A-37 | Bn | benzo[1,3]dioxol-5-yl | S | 2.74(dd, J=9.6, 13.8Hz, 1H), 2.98(d, J=5.4, 13.8Hz, 1H), 3.95(dt, J=5.1, 8.4Hz, 1H), 6.22(s, 2H), 7.10–7.23 (m, 6H), 7.67(d, J=1.5Hz, 1H), 7.75(d, J=8.4Hz, 2H), 7.81(dd, J=1.5, 8.4Hz, 1H), 8.06(d, J=8.4Hz, 2H), 8.51(d, J=9.0Hz, 1H), 12.81(br s, 1H) |
| 38 | A-38 | Bn | 3,4-dimethoxyphenyl | S | 2.75(dd, J=9.3, 13.8Hz, 1H), 2.98(d, J=5.7, 13.8Hz, 1H), 3.90(s, 3H), 3.91(s, 3H), 3.96(dt, J=5.4, 8.7Hz, 1H), 7.10–7.23(m, 5H), 7.24(d, J=8.4 Hz, 1H), 7.66(d, J=2.1Hz, 2H), 7.73–7.79(m, 2H), 7.83(dd, J=2.1, 8.4Hz, 1H), 8.09–8.15(m, 2H), 8.51(d, J=9.3 Hz, 1H), 12.79(br s, 1H) |
| 39 | A-39 | Bn | 3,4-dichlorophenyl | S | 2.74(dd, J=9.6, 13.8Hz, 1H), 2.99(d, J=5.4, 13.8Hz, 1H), 3.96(dt, J=5.1, 9.3Hz, 1H), 7.09–7.23(m, 5H), 7.24(d, J=8.4Hz, 1H), 7.76(d, J=8.7Hz, 2H), 7.96(d, J=8.4Hz, 2H), 8.12(d, J=8.7 Hz, 2H), 8.18(dd, J=2.1, 8.4Hz, 1H), 8.40(d, J=2.1Hz, 1H), 8.53(d, J=8.7 Hz, 1H), 12.70(br s, 1H) |
| 40 | A-40 | Bn | thiophen-2-yl | R | 2.74(dd, J=9.6, 13.8Hz, 1H), 2.98(dd, J=5.7, 13.8Hz, 1H), 3.95(dt, J=5.7, 8.7Hz, 1H), 7.10–7.22(m, 5H), 7.39(dd, J=3.9, 4.8Hz, 1H), 7.72–7.78 (m, 2H), 8.13(dd, J=1.5, 3.9Hz, 1H), 8.15(dd, J=1.5, 4.8Hz, 1H), 8.06–8.12(m, 2H), 8.52(d, J=8.7Hz, 1H), 12.80(br s, 1H) |
| 41 | A-41 | Bn | 5-methylthiophen-2-yl | R | 2.66(s, 3H), 2.74(dd, J=9.6, 13.8Hz, 1H), 2.98(dd, J=5.4, 13.8Hz, 1H), 3.95(m, 1H), 7.09–7.23(m, 6H), 7.74(d, J=8.7Hz, 2H), 7.94(d, J=3.6 Hz, 1H), 8.07(d, J=8.7Hz, 2H), 8.51(d, J=8.7Hz, 1H), 12.79(br s, 1H) |

TABLE 7

| Ex. No. | Compound No. | R⁷ | R⁸ | * | ¹H-NMR (DMSO-d₆) |
|---|---|---|---|---|---|
| 42 | A-42 | Bn | furan-2-yl | R | 2.74(dd, J=9.6, 13.8Hz, 1H), 2.99(dd, J=5.4, 13.8Hz, 1H), 3.96(dt, J=5.1, 9.0Hz, 1H), 6.90(dd, J=1.8, 3.9Hz, 1H), 7.10–7.22(m, 5H), 7.70(d, J=3.9 Hz, 1H), 7.75(d, J=8.4Hz, 2H), 8.09 (d, J=8.4Hz, 2H), 8.21(m, 1H), 8.51 (d, J=9.0Hz, 1H), 12.79(br s, 1H) |
| 43 | A-43 | Bn | pyridin-3-yl | R | 2.74(dd, J=9.6, 13.6Hz, 1H), 2.99(dd, J=5.4, 13.6Hz, 1H), 3.96(m, 1H), 7.05–7.3(5H), 7.71(d, J=5.2Hz, 1H), 7.77(d, J=8.4Hz, 2H), 8.14(d, J=8.4 Hz, 2H), 8.52(m, 1H), 8.59(m, 1H), 8.92(dd, J=1.4, 4.8Hz, 1H), 9.37(d, J=1.4Hz, 1H), 12.8(br s, 1H) |

TABLE 7-continued

| Ex. No. | Compound No. | R⁷ | R⁸ | * | ¹H-NMR (DMSO-d₆) |
|---|---|---|---|---|---|
| 44 | A-44 | Me | phenyl | R | 1.21(d, J=6.9Hz, 3H), 3.87(m, 1H), 7.66–7.73(m, 2H), 7.77(m, 1H), 8.02(d, J=8.1Hz, 2H), 8.20–8.25(m, 2H), 8.28(d, J=8.1Hz, 2H), 8.39(d, J=8.1Hz, 1H), 12.69(br s, 1H) |
| 45 | A-45 | Me | 4-F-phenyl | R | 1.20(d, J=7.2Hz, 3H), 3.87(m, 1H), 7.53(t, J=8.7Hz, 2H), 8.01(d, J=8.4 Hz, 2H), 8.23–8.32(m, 4H), 8.37(d, J=8.4Hz, 1H), 12.66(br s, 1H) |
| 46 | A-46 | Me | 4-Me-phenyl | S | 1.20(d, J=7.2Hz, 3H), 2.45(s, 3H), 3.86(m, 1H), 7.50(d, J=8.4Hz, 2H), 8.00(d, J=8.4Hz, 2H), 8.10(d, J=8.4Hz, 2H), 8.27(d, J=8.4Hz, 2H), 8.38(d, J=7.4Hz, 1H), 12.69(br, 1H) |
| 47 | A-47 | Me | 4-Et-phenyl | R | 1.21(d, J=7.2Hz, 3H), 1.24(t, J=7.5 Hz, 3H), 2.75(q, J=7.5Hz, 2H), 3.87(m, 1H), 7.53(d, J=8.7Hz, 2H), 8.01(d, J=8.1Hz, 2H), 8.13(d, J=8.7 Hz, 2H), 8.27(d, J=8.1Hz, 2H), 8.37(d, J=8.7Hz, 1H), 12.65(br s, 1H) |
| 48 | A-48 | Me | 4-nPr-phenyl | R | 0.93(t, J=7.2Hz, 3H), 1.21(d, J=6.9 Hz, 3H), 1.59–1.73(m, 2H), 2.70(t, J=7.5Hz, 2H), 3.87(m, 1H), 7.51(d, J=8.4Hz, 2H), 8.01(d, J=8.4Hz, 2H), 8.13(d, J=8.4Hz, 2H), 8.27(d, J=8.4 Hz, 2H), 8.37(d, J=8.4Hz, 1H), 12.66 (br s, 1H) |

TABLE 8

| Ex. No. | Compound No. | R⁷ | R⁸ | * | ¹H-NMR (DMSO-d₆) |
|---|---|---|---|---|---|
| 49 | A-49 | Me | 4-nPr-phenyl | S | 0.93(t, J=7.5Hz, 3H), 1.20(d, J=7.2 Hz, 3H), 1.58–1.73(m, 2H), 2.66(t, J=7.2Hz, 2H), 3.79–3.91(m, 1H), 7.63(d, J=7.8Hz, 2H), 8.00(d, J=8.4 Hz, 2H), 8.13(d, J=8.4Hz, 2H), 8.27(d, J=8.7Hz, 2H), 8.37(brs, 1H), 12.74(brs, 1H) |
| 50 | A-50 | Me | 4-O₂N-phenyl | R | 1.20(d, J=7.2Hz, 3H), 3.87(m, 1H), 7.99–8.05(m, 2H), 8.27–8.32(m, 2H), 8.39(d, J=9.0Hz, 1H), 8.46 and 8.50(ABq, J=9.6Hz, 4H), 12.66(br s, 1H) |
| 51 | A-51 | Me | 4-Ac-phenyl | R | 1.21(d, J=7.2Hz, 3H), 2.68(s, 3H), 3.87(m, 1H), 8.02(d, J=8.4Hz, 2H), 8.21(d, J=8.4Hz, 2H), 8.29(d, J=8.4 Hz, 2H), 8.35(d, J=8.4Hz, 2H), 8.40(d, J=8.1Hz, 1H), 12.68(br s, 1H) |
| 52 | A-52 | Me | 2-thienyl | R | 1.20(d, J=7.5Hz, 3H), 3.86(m, 1H), 7.39(dd, J=3.9, 4.8Hz, 1H), 7.97–8.03(m, 2H), 8.12(dt, J=3.9, 0.9Hz, 1H), 8.15(dd, J=0.9, 4.8Hz, 1H), 8.21–8.27(m, 2H), 8.37(d, J=8.4Hz, 1H), 12.66(br s, 1H) |
| 53 | A-53 | Me | 5-Me-2-thienyl | R | 1.20(d, J=7.5Hz, 3H), 2.60(s, 3H), 3.85(m, 1H), 7.11(d, J=3.9Hz, 1H), 7.94(d, J=3.9Hz, 1H), 7.96–8.01(m, 2H), 8.19–8.25(m, 2H), 8.39(d, J=8.7 Hz, 1H), 12.68(br s, 1H) |

TABLE 8-continued

| Ex. No. | Compound No. | $R^7$ | $R^8$ | * | $^1$H-NMR (DMSO-$d_6$) |
|---|---|---|---|---|---|
| 54 | A-54 | Me | 5-chloro-2-thienyl | R | 1.20(d, J=6.9Hz, 3H), 3.86(m, 1H), 7.46(d, J=4.2Hz, 1H), 7.99(d, J=8.7 Hz, 2H), 8.03(d, J=4.2Hz, 1H), 8.22(d, J=8.7Hz, 2H), 8.39(d, J=8.1 Hz, 1H), 12.65(br s, 1H) |
| 55 | A-55 | Me | 3-thienyl | R | 1.20(d, J=7.2Hz, 3H), 3.86(m, 1H), 7.78(dd, J=1.2, 5.1Hz, 1H), 7.90(dd, J=3.0, 5.1Hz, 1H), 7.97–8.03(m, 2H), 8.22–8.28(m, 2H), 8.38(d, J=7.8Hz, 1H), 8.71(dd, J=1.2, 3.0Hz, 1H), 12.67(br s, 1H) |
| 56 | A-56 | Me | 2-furyl | R | 1.20(d, J=7.5Hz, 3H), 3.86(m, 1H), 6.91(dd, J=1.8, 3.6Hz, 1H), 7.69(d, J=3.6Hz, 1H), 7.97–8.03(m, 2H), 8.22(dd, J=1.8, 3.6Hz, 1H), 8.22–8.27 (m, 2H), 8.39(d, J=8.7Hz, 1H), 12.64 (br s, 1H) |

TABLE 9

| Ex. No. | Compound No. | $R^7$ | $R^8$ | * | $^1$H-NMR (DMSO-$d_6$) |
|---|---|---|---|---|---|
| 57 | A-57 | H | 4-F-C$_6$H$_4$- | | 3.68(d, J=4.8Hz, 2H), 7.49–7.58(m, 2H), 8.02(d, J=8.7Hz, 2H), 8.26–8.31(m, 5H), 12.70(br s, 1H) |
| 58 | A-58 | H | 4-Br-C$_6$H$_4$- | | 3.68(d, J=4.8Hz, 2H), 7.90(d, J=8.4 Hz, 2H), 8.02(d, J=8.4Hz, 2H), 8.14(d, J=8.4Hz, 2H), 8.24–8.30(m, 3H), 12.68(br s, 1H) |
| 59 | A-59 | H | 4-Et-C$_6$H$_4$- | | 1.24(t, J=7.5Hz, 3H), 2.75(q, J=7.5 Hz, 2H), 3.68(d, J=8.1Hz, 2H), 7.53 (d, J=8.1Hz, 2H), 8.01(d, J=8.1 Hz, 2H), 8.13(d, J=8.4Hz, 2H), 8.27 (d, J=8.1Hz, 2H), 8.27(m, 1H), 12.75(br s, 1H) |
| 60 | A-60 | H | 4-$^i$Pr-C$_6$H$_4$- | | 1.27(d, J=6.9Hz, 6H), 3.04(m, 1H), 3.68(d, J=4.2Hz, 2H), 7.56(d, J=8.4 Hz, 2H), 8.02(d, J=8.4Hz, 2H), 8.14(d, J=8.4Hz, 2H), 8.23–8.32(m, 3H), 12.71(br s, 1H) |
| 61 | A-61 | H | 4-$^n$Pr-C$_6$H$_4$- | | 0.92(t, J=7.5Hz, 3H), 1.66(m, 2H), 2.69(t, J=7.8Hz, 2H), 3.68(d, J=4.8 Hz, 2H), 7.51(d, J=8.1Hz, 2H), 8.01(d, J=8.7Hz, 2H), 8.13(d, J=8.1 Hz, 2H), 8.27(d, J=8.7Hz, H), 8.27(m, 1H), 12.71(br s, 1H) |
| 62 | A-62 | H | 2-thienyl | | 3.67(d, J=4.4Hz, 2H), 7.39(m, 1H), 8.00(d, J=8.4Hz, 2H), 8.13(m, 2H), 12.6(br s, 1H) |
| 63 | A-63 | H | 5-Me-2-thienyl | | 2.60(s, 3H), 3.67(d, J=5.4Hz, 2H), 7.11(d, J=3.9Hz, 1H), 7.94(d, J=3.9 Hz, 1H), 7.99(d, J=8.1Hz, 2H), 8.22 (d, J=8.1Hz, 2H), 8.28(t, J=5.4Hz, 1H), 12.70(br s, 1H) |

TABLE 9-continued

| Ex. No. | Compound No. | R⁷ | R⁸ | * | ¹H-NMR (DMSO-d₆) |
|---|---|---|---|---|---|
| 64 | A-64 | Indol-3-yl methyl | 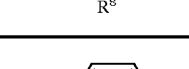 | R | 1.25(t, J=7.6Hz, 3H), 2.75(q, J=7.6 Hz, 2H), 2.88(dd, J=8.8, 14.2Hz, 1H), 3.10(dd, J=5.4, 14.3Hz, 1H), 3.98(m, 1H), 6.8–7.0(2H), 7.08(d, J=1.8Hz, 1H), 7.20(m, 1H), 7.33(m, 1H), 7.54 (d, J=8.2Hz, 2H), 7.69(d, J=8.4Hz, 2H), 8.00(d, J=8.0Hz, 2H), 8.14(d, J=8.2 Hz, 2H), 8.46(d, J=8.4Hz, 1H), 12.64(br s, 1H) |

TABLE 10

| Ex. No. | Compound No. | R⁷ | R⁸ | * | ¹H-NMR (DMSO-d₆) |
|---|---|---|---|---|---|
| 65 | A-65 | Indol-3-yl methyl | ⁿPr—⟨phenyl⟩— | R | 0.93(dt, J=1.2, 6.0Hz, 3H), 1.67(m, 2H), 2.70(t, J=6.9Hz, 2H), 2.89(dd, 8.4, 14.4Hz, 1H), 3.10(dd, J=5.4, 14.7 Hz, 1H), 3.98(m, 1H), 6.92(m, 2H), 7.09(s, 1H), 7.20(m, 1H), 7.33(d, J=7.8Hz, 1H), 7.52(d, J=7.2Hz, 2H), 7.69(d, J=7.5Hz, 2H), 8.0(d, J=7.5 Hz, 2H), 8.14(d, J=7.5Hz, 2H), 8.47(d, J=8.1Hz, 1H), 10.78(s, 1H), 12.72(br s, 1H) |
| 66 | A-66 | i-Bu | Cl—⟨phenyl⟩— | R | 0.73(d, J=6.6Hz, 3H), 0.83(d, J=6.6 Hz, 3H), 1.3–1.75(3H), 3.74(m, 1H), 7.76(d, J=8.8Hz, 2H), 7.99(d, J=8.4 Hz, 2H), 8.22(d, J=8.8Hz, 2H), 8.27(d, J=8.0Hz, 2H), 8.38(d, J=7.6 Hz, 1H), 12.61(br s, 1H) |
| 67 | A-67 | i-Bu | Me—⟨phenyl⟩— | S | 0.74(d, J=6.6Hz, 3H), 0.83(d, J=6.6 Hz, 3H), 1.38–1.50(m, 2H), 1.60(m, 1H), 2.45(s, 3H), 3.74(m, 1H), 7.49(d, J=8.1Hz, 1H), 7.98(d, J=8.1Hz, 1H), 8.11(d, J=8.1Hz, 2H), 8.26(d, J=8.1 Hz, 2H), 8.36(d, J=8.4Hz, 1H), 12.63(br, 1H) |

TABLE 11

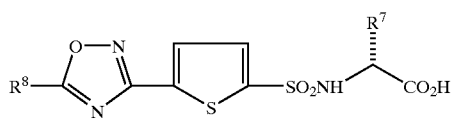

| Ex. No. | Compound No. | R⁷ | R⁸ | ¹H-NMR DMSO-d₆ |
|---|---|---|---|---|
| 68 | B-1 | i-Pr | F—⟨phenyl⟩— | 0.83(d, J=6.9 Hz, 3H), 0.88(d, J=6.9 Hz, 3H), 2.03(m, 1H), 3.68(m, 1H), 7.52(t, J=8.7 Hz, 2H), 7.67(d, J=3.9 Hz, 1H), 7.86(d, J=3.9 Hz, 1H), 8.25(dd, J=2.4, 8.7 Hz, 2H), 8.59(m, 1H), 12.74(br s, 1H). |
| 69 | B-2 | i-Pr | Et—⟨phenyl⟩— | 0.83(d, J=6.9 Hz, 3H), 0.88(d, J=6.9 Hz, 3H), 1.24(t, J=7.5 Hz, 3H), 2.03(m, 1H), 2.74(q, J=7.5 Hz, 1H), 3.66(m, 1H), 7.52(d, J=8.4 Hz, 2H), 7.66(d, J=3.9 Hz, 1H), 7.86(d, J=3.9 Hz, 1H), 8.10(d, J=8.4 Hz, 2H), 8.58(m, 1H), 12.77(br s, 1H). |

TABLE 11-continued

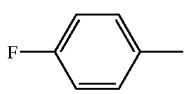

| Ex. No. | Compound No. | R⁷ | R⁸ | ¹H-NMR DMSO-d₆ |
|---|---|---|---|---|
| 70 | B-3 | Bn | 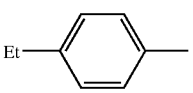 | 2.76(dd, J=9.6, 13.8 Hz, 1H), 3.03(dd, J=5.1, 13.8 Hz, 1H), 4.02(br s, 1H), 7.09–7.22(m, 5H), 7.40(d, J=3.9 Hz, 1H), 7.53(t, J=9.0 Hz, 2H), 7.71(d, J=3.9 Hz, 2H), 8.24–8.29(m, 2H), 8.87(d, J=8.7 Hz, 1H), 12.94(br s, 1H) |
| 71 | B-4 | Bn | 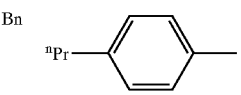 | 1.24(t, J=7.8 Hz, 3H), 2.71–2.81(m, 3H), 3.03(dd, J=4.8 13.5 Hz, 1H), 4.02 (br s, 1H), 7.08–7.22(m, 5H), 7.40(d, J=4.2 Hz, 1H), 7.53(d, J=8.4 Hz, 2H), 7.71(d, J=3.6 Hz, 1H), 8.10(d, J=8.1 Hz, 2H), 8.85(br s, 1H), 12.91(br s, 1H) |
| 72 | B-5 | Bn | 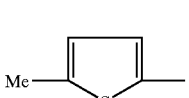 | 0.92(t, J=7.5 Hz, 3H), 1.59–1.72(m, 2H), 2.69–2.80(m, 3H), 3.03(dd, J=5.1, 13.8 Hz, 1H), 4.02(br s, 1H), 7.08–7.22(m, 5H), 7.40(d, J=3.9 Hz, 1H), 7.51(d, J=8.4 Hz, 2H), 7.71(d, J=3.9 Hz, 1H), 8.10(d, J=8.4 Hz, 2H), 8.86 (d, J=8.4 Hz, 1H), 12.93(br s, 1H) |
| 73 | B-6 | Bn | 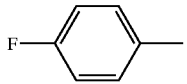 | 2.06(s, 3H), 2.75(dd, J=9.6, 14.0 Hz, 1H), 3.02(dd, J=5.2, 14.0 Hz, 1H), 4.00(br s, 1H), 7.07–7.22 (m, 6H), 7.38(d, J=3.6 Hz, 1H), 7.68(d, J=4.0 Hz, 1H), 7.94(d, J=4.2 Hz, 1H) 8.85(br s, 1H), 12.80(br s, 1H) |
| 74 | B-7 | Me | 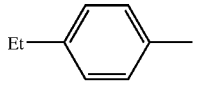 | 1.26(d, J=7.2 Hz, 3H), 3.93(q, J=7.2 Hz, 1H), 7.53(t, J=9.0 Hz, 2H), 7.70(d, J=3.9 Hz, 1H), 7.88(d, J=3.9 Hz, 1H), 8.26(dd, J=5.4, 9.0 Hz, 2H), 8.72(m, 1H), 12.62(br s, 1H). |

TABLE 12

| Ex. No. | Compound No. | R⁷ | R⁸ | ¹H-NMR (DMSO-d₆) |
|---|---|---|---|---|
| 75 | B-8 | Me | 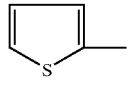 | 1.24(m, 5H), 2.74(q, J=7.5 Hz, 2H), 3.94(m, 1H), 7.52(d, J=8.1 Hz, 2H), 7.69(d, J=3.9 Hz, 1H), 7.87(d, J=3.9 Hz, 1H), 8.10(d, J=8.1 Hz, 2H), 8.72(m, 1H), 12.77(br s, 1H). |
| 76 | B-9 | Me | 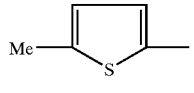 | 1.25(d, J=7.2 Hz, 3H), 3.93(m, 1H), 7.38(dd, J=3.9, 5.1 Hz, 1H), 7.68(d, J=3.9 Hz, 1H), 7.86(d, J=3.9 Hz, 1H), 8.12(dd, J=1.2, 3.9 Hz, 1H), 8.16(dd, J=1.2, 5.1 Hz, 1H), 8.70(m, 1H), 12.73 (br s, 1H). |
| 77 | B-10 | Me | 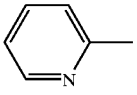 | 1.24(d, J=7.2 Hz, 3H), 2.60(d, J=0.6 Hz, 3H), 3.89–3.96(m, 1H), 7.10–7.11(m, 1H), 7.67(d, J=3.9 Hz, 1H), 7.84(d, J=3.9 Hz, 1H), 7.93(d, J=3.6 Hz, 1H), 8.69(br s, 1H) |
| 78 | B-11 | Me | 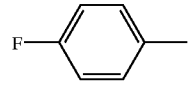 | 1.26(d, J=7.4 Hz, 3H), 3.94(br s, 1H), 7.70–7.79(m, 2H), 7.91(d, J=4.2 Hz, 1H), 8.14(dt, J=1.8, 8.0 Hz, 1H), 8.33 (d, J=7.6 Hz, 1H), 8.72 (br s, 1H), 8.87 (d, J=4.4 Hz, 1H), 12.80 (br s, 1H) |
| 79 | B-12 | Indol-3-yl methyl |  | 2.90(dd, J=6.0, 14.4 Hz, 1H), 3.14 (dd, J=4.5, 14.4 Hz, 1H), 4.02(m, 1H), 6.9–7.6(m, 11H), 8.26(m, 3H), 10.76(s, 1H). |

TABLE 12-continued

| Ex. No. | Compound No. | R⁷ | R⁸ | ¹H-NMR (DMSO-d₆) |
|---|---|---|---|---|
| 80 | B-13 | Indol-3-yl methyl | Et—⟨phenyl⟩ | 1.24(t, J=7.5 Hz, 3H), 2.75(q, J=7.5 Hz, 2H), 2.91(dd, J=9.0, 14.7 Hz, 1H), 3.13(dd, J=5.4, 14.7 Hz, 1H), 4.04(m, 1H), 6.92(m, 2H), 7.10(d, J=2.1 Hz, 1H), 7.17(m, 1H), 2.30(d, J=3.9 Hz, 1H), 7.39(m, 1H), 7.53(d, J=3.9 Hz, 1H), 7.53(d, J=8.4 Hz, 2H), 8.11(d, J=8.4 Hz, 2H), 8.79(m, 1H), 10.77(s, 1H), 12.84(br s, 1H). |
| 81 | B-14 | H | F—⟨phenyl⟩ | 3.76(s, 2H), 7.53(t, J=8.7 Hz, 1H), 7.72(d, J=3.9 Hz, 1H), 7.88(d, J=4.2 Hz, 1H), 8.23–8.28(m, 2H), 8.60(br s, 1H), 12.79(br s, 1H) |
| 82 | B-15 | H | Me—⟨phenyl⟩ | 2.44(s, 3H), 3.76(s, 2H), 7.49(d, J=7.8 Hz, 2H), 7.72(d, J=3.6 Hz, 2H), 7.88(d, J=4.2 Hz, 2H), 8.07(d, J=8.1 Hz, 2H), 8.62(br s, 1H), 12.80(br s, 1H) |
| 83 | B-16 | H | Et—⟨phenyl⟩ | 1.24(t, J=7.5 Hz, 3H), 2.71–2.78(m, 2H), 3.76(s, 2H), 7.52(d, J=7.8 Hz, 2H), 7.72(d, J=3.9 Hz, 1H), 7.88(d, J=4.2 Hz, 1H), 8.10(d, J=8.1 Hz, 2H), 8.60(br s, 1H), 12.80(br s, 1H) |

Test Example

Test Example 1

Isolation and Purification of MMP-2

MMP-2 was purchased from Calbiochem-Novabiochem International, Inc.

Test Example 2

Assay for Inhibitory Activities on MMP-2

The enzymatic activity on MMP-2 was analyzed by the method described in "C. Graham Knight, Frances Willenbrock and Gillian Murphy: A novel coumarin-labelled peptide for sensitive continuous assays of the matrix metalloproteinases: FEBS LETT., 296, (1992), 263–266". The substrate: MOCAc-Pro-Leu-Gly-Leu-A₂Pr(DNP)-Ala-Arg-NH₂ was purchased from Peptide Institute, Inc., Osaka, Japan.

The measurement of the inhibitory activities (IC₅₀) was carried out by the following four methods;

A) Reaction with substrate, enzyme (MMPs) and inhibitor
B) Reaction with substrate and inhibitor, without enzyme
C) Reaction with substrate and enzyme (MMPs), without inhibitor
D) Reaction with substrate only IC₅₀ values were calculated by using the following formula and each fluorescence values of above four methods (A to D).

% inhibition={1-(A-B)/(C-D)}×100

IC₅₀ means the concentration required to inhibit 50% of the enzyme activity.

The results are shown in Table 13.

TABLE 13

| Compound No. | IC₅₀ (μM) | Compound No. | IC₅₀ (μM) | Compound No. | IC₅₀ (μM) |
|---|---|---|---|---|---|
| A-1 | 0.00462 | A-30 | 0.0398 | A-57 | 0.181 |
| A-2 | 0.00575 | A-31 | 0.00498 | A-58 | 0.0534 |
| A-3 | 0.00124 | A-32 | 0.00445 | A-59 | 0.0200 |
| A-4 | 0.00123 | A-33 | 0.0300 | A-60 | 0.0143 |
| A-5 | 0.00668 | A-34 | 0.0131 | A-61 | 0.0157 |
| A-6 | 0.0139 | A-35 | 0.0144 | A-62 | 0.196 |
| A-7 | 0.0265 | A-36 | 0.0380 | A-63 | 0.0339 |
| A-8 | 0.0119 | A-37 | 0.0202 | A-64 | 0.00139 |
| A-9 | 0.00604 | A-38 | 0.506 | A-65 | 0.00166 |
| A-10 | 0.00917 | A-39 | 0.0807 | A-66 | 0.0376 |
| A-11 | 0.0186 | A-40 | 0.0310 | A-67 | 0.124 |
| A-12 | 0.0516 | A-41 | 0.00559 | B-1 | 0.0677 |
| A-13 | 0.0852 | A-42 | 0.0470 | B-2 | 0.00539 |
| A-16 | 0.0264 | A-43 | 0.171 | B-3 | 0.223 |
| A-17 | 0.0155 | A-44 | 0.045 | B-4 | 0.0178 |
| A-18 | 0.00462 | A-45 | 0.0310 | B-5 | 0.0361 |
| A-19 | 0.114 | A-46 | 0.458 | B-6 | 0.0265 |
| A-20 | 0.000883 | A-47 | 0.00463 | B-7 | 0.0397 |
| A-21 | 0.126 | A-48 | 0.00117 | B-8 | 0.00290 |
| A-22 | 0.0407 | A-49 | 0.126 | B-9 | 0.0280 |
| A-23 | 0.339 | A-50 | 0.0126 | B-10 | 0.00629 |
| A-24 | 0.00288 | A-51 | 0.00321 | B-11 | 0.614 |
| A-25 | 0.0474 | A-52 | 0.0368 | B-12 | 0.0290 |
| A-26 | 0.00672 | A-53 | 0.00874 | B-13 | 0.00408 |
| A-27 | 0.0603 | A-54 | 0.0124 | B-14 | 0.224 |
| A-28 | 0.0256 | A-55 | 0.0503 | B-15 | 0.0390 |
| A-29 | 0.0279 | A-56 | 0.0705 | B-16 | 0.0126 |

Formulation Example

Formulation Example 1

Granules are prepared using the following ingredients.

| Ingredients | |
|---|---|
| The compound represented by the formula (I) | 10 mg |
| Lactose | 700 mg |
| Corn starch | 274 mg |
| HPC-L | 16 mg |
| | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2

Powders for filling capsules are prepared using the following ingredients.

| Ingredients | |
|---|---|
| The compound represented by the formula (I) | 10 mg |
| Lactose | 79 mg |
| Corn starch | 10 mg |
| Magnesium stearate | 1 mg |
| | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3

Granules for filling capsules are prepared using the following ingredients.

| Ingredients | |
|---|---|
| The compound represented by the formula (I) | 15 mg |
| Lactose | 90 mg |
| Corn starch | 42 mg |
| HPC-L | 3 mg |
| | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation 4

Tablets are prepared using the following ingredients.

| Ingredients | |
|---|---|
| The compound represented by the formula (I) | 10 mg |
| Lactose | 90 mg |
| Microcrystal cellulose | 30 mg |
| CMC-Na | 15 mg |
| Magnesium stearate | 5 mg |
| | 150 mg |

The compound represented by the formula (I), lactose, microcrystal cellulose, and CMC-Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

INDUSTRIAL APPLICABILITY

The sulfonamide derivatives of the present invention have an inhibiting activities of the metalloprotease and are useful as the treating or preventing agent of cancer, nephritis, osteoarthrosis, heart failure and rheumatoid arthritis.

What is claimed is:

1. A compound of the formula (I):

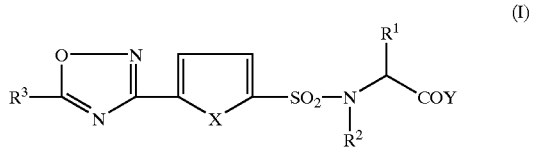

(I)

wherein
$R^1$ and $R^2$ are each independently hydrogen atom, optionally substituted lower alkyl, optionally substituted aryl, optionally substituted aralkyl, optionally substituted heteroaryl, or optionally substituted heteroarylalkyl;
$R^3$ is optionally substituted lower alkyl, optionally substituted cycloalkyl, lower alkyloxy, optionally substituted aryl, optionally substituted aralkyl, optionally substituted heteroaryl, optionally substituted heteroarylalkyl, optionally substituted non-aromatic heterocyclic group, unsubstituted or substituted amino, or halogen; and
X is —CH=CH—, —O—, or —S—;
Y is —NHOH, hydroxy, or lower alkyloxy,
its optically active substance, its pharmaceutically acceptable salt, or its solvate.

2. A compound of the formula (II):

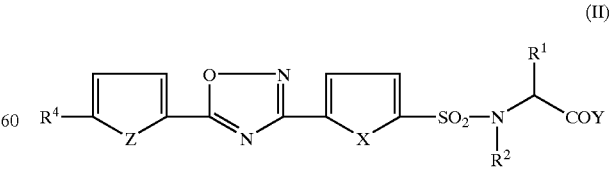

(II)

wherein
$R^1$, $R^2$, X and Y are as defined in claim 1;
$R^4$ is hydrogen atom, optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino group, azo group, or optionally substituted ureide; and Z is —CH=CH—, —O—, or —S—, its optically active substance, its pharmaceutically acceptable salt, or its solvate.

3. A compound of the formula (III):

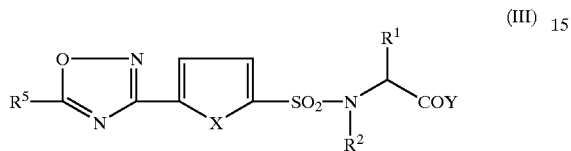

(III)

wherein $R^1$, $R^2$, X, and Y are as defined in claim 1; and
$R^5$ is optionally substituted alkyl, optionally substituted aralkyl, optionally substituted heteroaryl alkyl, lower alkyloxy, unsubstituted or substituted amino, or halogen, its optically active substance, its pharmaceutically acceptable salt, or its solvate.

4. A compound of the formula (IV):

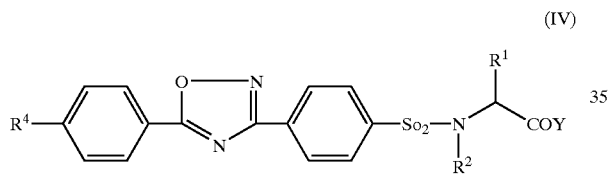

(IV)

wherein $R^1$, $R^2$, and Y are as defined in claim 1, and $R^4$ is hydrogen atom, optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino group, azo group, or optionally substituted ureide, its optically active substance, its pharmaceutically acceptable salt, or its solvate.

5. A compound of the formula (V):

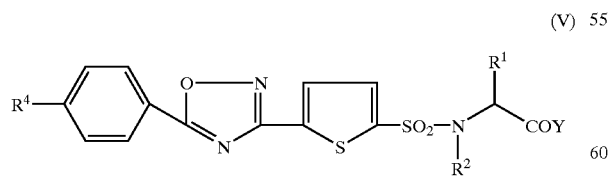

(V)

wherein $R^1$, $R^2$, and Y are as defined in claim 1, and $R^4$ is hydrogen atom, optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino group, azo group, or optionally substituted ureide, its optically active substance, its pharmaceutically acceptable salt, or its solvate.

6. A compound of the formula (VI):

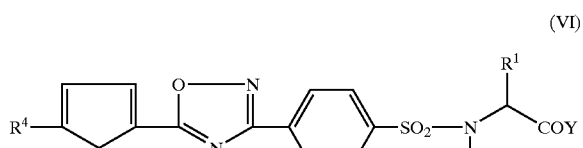

(VI)

wherein $R^1$, $R^2$, and Y are as defined in claim 1, and $R^4$ is hydrogen atom, optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino group, azo group, or optionally substituted ureide, its optically active substance, its pharmaceutically acceptable salt, or its solvate.

7. A compound of the formula (VII):

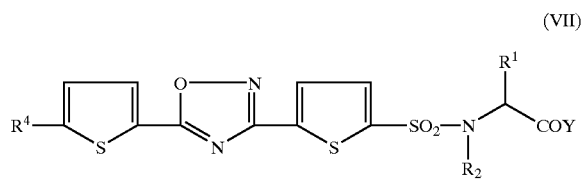

(VII)

wherein $R^1$, $R^2$, and Y are as defined in claim 1, and $R^4$ is hydrogen atom, optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino group, azo group, or optionally substituted ureide, its optically active substance, its pharmaceutically acceptable salt, or its solvate.

8. A compound of claim 1, wherein Y is hydroxy, its optically active substance, its pharmaceutically acceptable salt, or its solvate.

9. A compound of claim 1, wherein $R^2$ is hydrogen atom, its optically active substance, its pharmaceutically acceptable salt, or its solvate.

10. A compound of claim 1, wherein $R^1$ is hydrogen atom, optionally substituted lower alkyl, optionally substituted aralkyl, or optionally substituted heteroarylalkyl, its optically active substance, its pharmaceutically acceptable salt, or its solvate.

11. A compound of claim 1, wherein $R^1$ is hydrogen atom, methyl, isopropyl, isobutyl, n-butyl, 2-methylthioethyl, phenylmethyl, or indol-3-ylmethyl, its optically active substance, its pharmaceutically acceptable salt, or its solvate.

12. A pharmaceutical composition containing a compound of claim 1.

13. A pharmaceutical composition containing a compound of claim 1 and a pharmaceutically acceptable carrier.

14. A method of inhibiting metalloproteinase comprising administering to a subject in need thereof an effective amount of a compound of claim 1 and a pharmaceutically acceptable carrier.

15. A method of inhibiting matrix metalloproteinase comprising administering to a subject in need thereof an effective amount of a compound of claim 1 and a pharmaceutically acceptable carrier.

16. A method of treating cancer which comprises administering to a subject in need thereof an effective amount of a compound of claim 1 and a pharmaceutically acceptable carrier.

17. A method of treating nephritis which comprises administering to a subject in need thereof an effective amount of a compound of claim 1 and a pharmaceutically acceptable carrier.

18. A method of treating osteoarthritis which comprises administering to a subject in need thereof an effective amount of a compound of claim 1 and a pharmaceutically acceptable carrier.

19. A method of treating cardiac insufficiency which comprises administering to a subject in need thereof an effective amount of a compound of claim 1 and a pharmaceutically acceptable carrier.

20. A method of treating rheumatoid arthritis which comprises administering to a subject in need thereof an effective amount of a compound of claim 1 and a pharmaceutically acceptable carrier.

21. A compound of the formula (VIII):

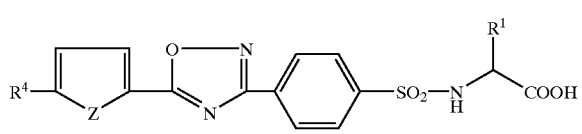

(VIII)

wherein
$R^1$ is hydrogen atom, methyl, isopropyl, isobutyl, n-butyl, 2-methyl thioethyl, phenylmethyl or indol-3-yl-methyl;
$R^4$ is hydrogen atom, optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, unsubstituted or substituted amino, unsubstituted or substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino, azo group, or optionally substituted ureide;
Z is —CH=CH—, —O—, or —S—,
its optically active form, its pharmaceutically acceptable salt, or its solvate.

22. A compound of the formula (VIII):

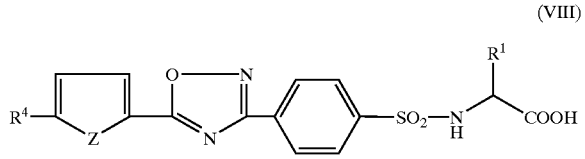

(VIII)

wherein
$R^1$ is hydrogen atom, methyl, isopropyl or phenylmethyl;
$R^4$ is hydrogen atom or optionally substituted lower alkyl,
Z is —CH=CH—, —O—, or —S—,
is optically active form, its pharmaceutically acceptable salt, or its solvate.

\* \* \* \* \*